US00PP35950P2

(12) United States Plant Patent
Boxriker

(10) Patent No.: US PP35,950 P2
(45) Date of Patent: Jul. 2, 2024

(54) ***OSTEOSPERMUM* PLANT NAMED 'KLEOE22715'**

(50) Latin Name: ***Osteospermum ecklonis* Norl.**
Varietal Denomination: KLEOE22715

(71) Applicant: KLEMM + SOHN GMBH & CO. KG, Stuttgart (DE)

(72) Inventor: Maike Boxriker, Stuttgart (DE)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 18/220,517

(22) Filed: Jul. 11, 2023

(51) Int. Cl.
*A01H 5/02* (2018.01)
*A01H 6/14* (2018.01)

(52) U.S. Cl.
USPC ..... Plt./360

(58) Field of Classification Search
USPC ..... Plt./360
CPC ..... A01H 5/02; A01H 5/00; A01H 6/14
See application file for complete search history.

(56) References Cited

U.S. PATENT DOCUMENTS

PP27,268 P2 * 10/2016 Klemm ..... A01H 6/14
Plt./360

OTHER PUBLICATIONS

BFG Spring Trials 2023 Report retrieved on Oct. 17, 2023 at https://www.bfgsupply.com/media/7520/2023-pc-spring-trials_web.pdf, 2 cover pages, pp. 12-16, 2 back pages. (Year: 2023).*
Dadpour et al. Inflorescence and floral ontogeny in *Osteospermum ecklonis* (Asteraceae) Botany, vol. 89: 605-614, 2011. (Year: 2011).*
Selecta One Zion *Osteospermum* Series retrieved on Oct. 17, 2023 at https://www.selectanorthamerica.com/SpringPlants/SeriesInfo/?phid=046105136051872, 2 pp. (Year: 2023).*

* cited by examiner

*Primary Examiner* — June Hwu
(74) *Attorney, Agent, or Firm* — Weatherly IP Solutions, LLC; James M. Weatherly

(57) ABSTRACT

A new *Osteospermum* plant particularly distinguished by pink flowers with white rings and good branching, is disclosed.

1 Drawing Sheet

Genus and species: *Osteospermum ecklonis* Norl.
Variety denomination: 'KLEOE22715'.

BACKGROUND OF THE NEW PLANT

The present invention comprises a new and distinct variety of *Osteospermum*, botanically known as *Osteospermum ecklonis* Norl., and hereinafter referred to by the variety name 'KLEOE22715'. 'KLEOE22715' originated from a cross-pollination conducted in Summer through Autumn 2018 in Nairobi, Kenya between the proprietary female *Osteospermum* variety 'OE-2017-4277' (unpatented) and the proprietary male *Osteospermum* variety 'OE-2016-3228' (unpatented).

The seeds from the cross were collected and in winter of 2018 and sown in Stuttgart, Germany and the plants were grown for evaluation. An individual plant designated 'KLEOE22715' was selected in May of 2019 in Stuttgart, Germany. In May of 2019 'KLEOE22715' was first vegetatively propagated by vegetative terminal cuttings in Stuttgart, Germany. 'KLEOE22715' was found to reproduce true to type in successive generations of asexual propagation via vegetative cuttings.

SUMMARY

The following are the most outstanding and distinguishing characteristics of this new variety when grown under normal horticultural practices in Stuttgart, Germany.

1. Single, pink flowers with white rings at the center of the flowers; and
2. Good branching.

DESCRIPTION OF THE PHOTOGRAPH

This new *Osteospermum* plant is illustrated by the accompanying photograph which shows a close-up the foliage, buds, and mature flower. The photograph is of a 12-week-old plant grown outdoors in Stuttgart, Germany in June 2022. The colors shown are as true as can be reasonably obtained by conventional photographic procedures.

DESCRIPTION OF THE NEW VARIETY

The following detailed descriptions set forth the distinctive characteristics of 'KLEOE22715'. The data which define these characteristics were collected in Stuttgart Germany in May 2023 on plants potted in week 8. Color references are to The R.H.S. Colour Chart of The Royal Horticultural Society of London (R.H.S.), 5$^{th}$ edition (2007).

Classification:
*Family*.—Asteraceae.
*Botanical*.—*Osteospermum ecklonis* Norl.
*Common*.—*Osteospermum*.
*Designation*.—'KLEOE22715'.

Parentage:
*Female parent*.—The proprietary female *Osteospermum* variety 'OE-2017-4277' (unpatented).

*Male parent*.—The proprietary male *Osteospermum* variety 'OE-2016-3228' (unpatented).

Plant:

*Form and habit*.—Herbaceous perennial but usually cultivated as an annual; not frost resistant.

*Growth habit*.—Upright.

*Branching habit*.—Normal.

*Height* (*from top of soil, including inflorescence*).—17.0 cm.

*Width* (*including inflorescences*).—21.0 cm.

*Propagation*.—Vegetative terminal cuttings.

*Time to produce a finished flowering plant*.—10 to 17 weeks.

*Time to initiate and develop roots*.—4 weeks.

*Root description*.—Fine, white (RHS 155C).

Stems:

*Total number of branches per plant* (*calculated at the base of the plant*).—6.

*Length*.—11.0 cm.

*Diameter*.—0.3 cm.

*Internode length*.—0.9 cm.

*Color*.—RHS 145A.

*Texture*.—Smooth.

*Anthocyanin*.—Absent.

Leaves:

*Arrangement*.—Alternate.

*Shape*.—Obovate.

*Apex*.—Acute.

*Base*.—Acute.

*Margin*.—Serrate.

*Margin indentation*.—Medium.

*Immature color*.—Upper surface: RHS 137B. Lower surface: RHS 138A.

*Mature color*.—Upper surface: RHS N137A. Lower surface: RHS 147B.

*Length*.—4.0 cm.

*Width*.—2.2 cm.

*Texture and appearance*.—Upper surface: Leathery. Lower surface: Leathery with fine hairs.

*Petioles*.—Absent.

*Venation pattern*.—Pinnate.

*Venation color*.—Upper surface: RHS 144A. Lower surface: RHS 144A.

Flower buds:

*Shape*.—Round.

*Length*.—0.9 cm.

*Diameter*.—1.0 cm.

*Color* (*at tight bud just before the ray florets unfold*).—RHS 145A.

Inflorescence:

*Type*.—Composite, single.

*Blooming habit*.—Upright with longer flower stems.

*Quantity of inflorescences per plant*.—6 at the time of evaluation of the plant; quantity depends on the stage of the plant and the environmental conditions.

*Lastingness of the inflorescences on the plant*.—10 to 15 days.

*Fragrance*.—Slightly present; fresh.

*Inflorescence diameter*.—7.3 cm.

*Inflorescence depth*.—0.5 cm.

*Disc diameter*.—1.4 cm.

Disc floret:

*Quantity per inflorescence*.—About 100.

*Shape*.—Tubular.

*Tube color*.—Closed: RHS 155A. Mature: RHS 155A.

*Length*.—0.5 cm.

*Diameter* (*at apex*).—0.1 cm.

*Apex*.—Acute.

*Apex color*.—RHS 159A.

*Base*.—Acute.

*Base color*.—RHS 157A.

*Margin*.—Entire.

Ray floret:

*Quantity per inflorescence*.—22.

*Shape*.—Oblanceolate.

*Color*.—Upper surface: RHS 70A with RHS NN155A ring (at the time of evaluation of the plant) and broad RHS N80B center with very weak longitudinal stripes. Lower surface: RHS 1D with RHS N137A light stripes.

*Length*.—3.5 cm.

*Width*.—0.9 cm.

*Apex*.—Obtuse.

*Base*.—Acute.

*Margin*.—Entire.

*Texture* (*upper and lower surfaces*).—Smooth.

*Peduncle*.—Length: 3.4 cm. Diameter: 0.2 cm. Texture: Smooth with hairs. Color: RHS 144B.

Phyllaries:

*Texture*.—Smooth with fine hairs.

*Color*.—RHS 143B.

*Arrangement*.—Single.

*Observed quantity per plant*.—21.

*Shape*.—Lanceolate.

*Color*.—Upper surface: RHS 143B. Lower surface: RHS 145A.

*Length*.—1.0 cm.

*Width*.—0.2 cm.

*Apex*.—Acute.

*Base*.—Obtuse.

*Margin*.—Entire.

*Texture*.—Upper surface: Smooth with fine hairs. Lower surface: Smooth.

Reproductive organs:

*Androecium location*.—On the disc floret.

*Stamens*.—Quantity: Numerous, 50-100. Shape: Filamentous. Filament length: 0.4 cm. Filament diameter: Less than 0.1 cm. Anther: Shape: Lanceolate. Color: RHS N77A. Length: 0.1 cm. Diameter: Less than 0.1 cm. Pollen: Color: RHS 21A. Amount: Moderate.

*Gynoecium location*.—On the base of the ray florets and disc florets.

*Pistils*.—Number: Numerous, 50-100. Length: 0.3 cm. Diameter: Less than 0.1 cm.

*Stigma*.—Color: RHS N77A. Shape: Filamentous. Length: 0.2 cm. Diameter: Greater than 0.1 cm.

*Style*.—Color: RHS N77A. Length: 0.1 cm. Diameter: Less than 0.1 cm.

Fruit and seed set: None observed.

Disease and pest/insect resistance: No disease and pest/insect resistance observed.

COMPARISON WITH PARENTAL LINES AND KNOWN VARIETY

'KLEOE22715' is a distinct variety of *Osteospermum* and is distinguished from its parents as described in Table 1.

TABLE 1

| Comparison with Parental Lines | | | |
|---|---|---|---|
| Characteristic | 'KLEOE22715' | Female Parent | Male Parent |
| Flower filling | Single | Double | Single |
| Flower color | Pink with white ring | Pink with yellow filling | Pink-purple with pink center |

'KLEOE22715' is most similar to the commercial *Osteospermum* variety 'KLEOE19396' (U.S. Plant Pat. No. 31,026). Differences between the varieties are described in Table 2.

TABLE 2

| Comparison with Similar Variety | | |
|---|---|---|
| Characteristic | 'KLEOE22715' | 'KLEOE19396' |
| Flower color | Pink with white ring | Orange with purple center |
| Branching | Good | Branching is not as good as 'KLEOE22715' |

I claim:

1. A new and distinct cultivar of *Osteospermum* Plant Named 'KLEOE22715' as described and illustrated herein.

* * * * *

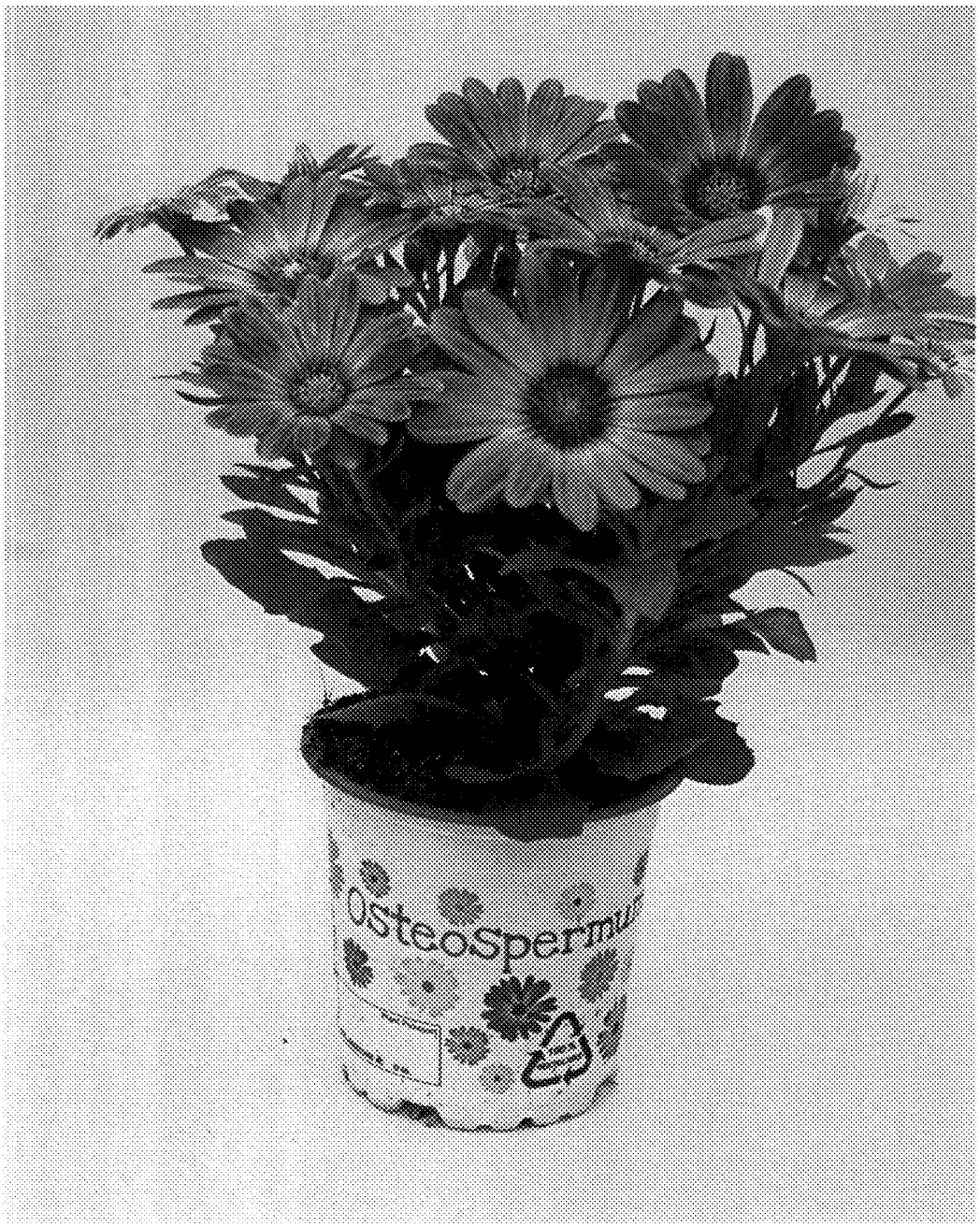
Osteospermum